United States Patent [19]
Davis et al.

[11] Patent Number: 5,460,599
[45] Date of Patent: Oct. 24, 1995

[54] ORTHOPEDIC HINGE ASSEMBLY FOR A LEG BRACE

[75] Inventors: Kenneth P. Davis, Wycombe; Peter I. Davis, Sunbury-on-Thames, both of England

[73] Assignee: Orthomerica Products, Inc., Newport Beach, Calif.

[21] Appl. No.: 249,527

[22] Filed: May 26, 1994

[51] Int. Cl.$^6$ ........................................... A61F 5/00
[52] U.S. Cl. .................. 602/26; 602/16; 602/20; 602/23; 602/27
[58] Field of Search .................. 602/5, 16, 23, 602/26; 623/16, 20, 127

[56] References Cited

U.S. PATENT DOCUMENTS

| | | | |
|---|---|---|---|
| 2,545,843 | 3/1951 | Cohan. | |
| 3,528,412 | 9/1970 | McDavid. | |
| 3,779,654 | 12/1973 | Horne. | |
| 3,902,482 | 9/1975 | Taylor. | |
| 4,088,130 | 5/1978 | Applegate | 602/26 X |
| 4,337,764 | 7/1982 | Lerman. | |
| 4,340,041 | 7/1982 | Frank | 602/26 X |
| 4,531,515 | 7/1985 | Rolfes. | |
| 4,881,299 | 11/1989 | Young et al.. | |
| 4,928,676 | 5/1990 | Pansiera. | |
| 4,982,734 | 1/1991 | Morris | 602/26 X |
| 5,000,170 | 3/1991 | Young et al.. | |
| 5,038,765 | 8/1991 | Young et al.. | |
| 5,039,247 | 8/1991 | Young et al.. | |
| 5,052,379 | 10/1991 | Airy et al. | 602/26 |
| 5,105,805 | 4/1992 | LaPointe et al. | 602/16 |
| 5,107,824 | 4/1992 | Rogers et al. | 602/26 X |
| 5,188,584 | 2/1993 | Petrofsky et al. | 602/16 |
| 5,399,154 | 3/1995 | Kipnis et al. | 602/16 X |

OTHER PUBLICATIONS

The "ezy wrap 1267" Hinged Knee Brace.
Bledsoe Brace Systems Catalog.
The Sentry Post–Op Knee Brace.
Matrix Medical Corporation CKM Brace #89.
Donjoy R.O.M. 4–Point Splint.
Donjoy Cool R.O.M. Splint.
Donjoy Post–Op/Rehab Braces, Nov. 1991.
Donjoy Catalog 1989.

*Primary Examiner*—Richard J. Apley
*Assistant Examiner*—Kim M. Lee
*Attorney, Agent, or Firm*—Price, Gess & Ubell

[57] ABSTRACT

An orthopedic hinge assembly for connecting an upper and lower portion of a brace, such as a knee brace, includes a hinge housing member with an abductor member movably mounted on the housing member. A pair of adjuster members are also mounted to the housing member and a stop member attached to the abductor member extends through arcuate apertures on the adjuster members. The adjuster members can have outer indentations and manually operable fastener assembly can fix or release the respective adjuster members so that they can be set to a desired position to define the limits of movement of the abductor member and thereby control flexion and extension of the patient's leg.

28 Claims, 6 Drawing Sheets

ORTHOPEDIC HINGE ASSEMBLY FOR A LEG BRACE

BACKGROUND OF THE INVENTION

1. Field of the Invention

The present invention is directed to an economical orthopedic hinge assembly for interconnecting an upper portion and a lower portion of a brace and more particularly to an improved hinge assembly which permits a precise adjustment of flexion and extension of a knee hinge brace.

2. Description of Related Art

A large number of different forms of orthopedic and orthotic hinge assemblies have been used for interconnecting component parts of an orthosis. Injuries associated with a knee are relatively common and are frequently related to both industrial and sports activities. A knee hinge brace is used for postoperative management and rehabilitation after cruciate and collateral ligament repair or reconstruction. Knee braces are used for patellar fractures, dislocations, and realignment procedures and both post-injury and preventive injury protection that would benefit from a controlled and limited movement of the joint, As can be appreciated, both cost and weight are factors in providing an effective knee hinge assembly for such an orthopedic brace, The orthopedic hinge assembly is provided adjacent the joint of the patient, such as a knee, to control the limits of movements of the leg and to partially support the weight of the patient across the natural knee joint of the patient. The actual brace portions attached to the patient can consist of cast material, or plastic shell components which are usually formed as two separate parts and interconnected by means of the hinge assembly. Ideally, the orthopedic brace should be adjustable so that it can be locked at any angle or range of movement without the need for elaborate tools.

Brace thigh and calf components can be formed of a polyethylene shell formed with neoprene material, One or more hinge assemblies can interconnect the brace components to permit the abduction flexion and extension required for the specific patient. Numerous elaborate schemes of relative expensive hinge assemblies have been proposed and touted in he medical and sport field. Usually, a joint assembly will permit a two-dimensional movement of an abductor brace portion and will require the setting of screws to define the movement of the abductor portion, which usually requires the services of a technician in this field.

There is still a demand in the orthopedic field to provide an improved economically constructed orthopedic hinge assembly that can provide an alternative to most of the knee hinge assembly requirements that are presently demanded by patients.

OBJECTS AND SUMMARY OF THE INVENTION

The present invention provides an orthopedic hinge assembly for interconnecting an upper portion and a lower portion of a brace, such as knee orthosis including an upper pair of modular thigh shells and a lower pair of modular calf shells. A hinge assembly can be attached to extension plates or bars which in turn can be adjustably attached to the respective upper and lower portions of the brace assembly.

A hinge housing member can be formed from a pair of flat aluminum plates that can be respectively connected to an extension plate or bar. Alternatively, the hinge housing member can be formed by a casting procedure as a unitary member having a central cavity. A pair of adjuster members of a flat disc configuration can be mounted to the housing member. Each of the adjuster members can have complementary perimeter indentations or gear teeth on at least a portion of their outer surface. The abductor member can also be movably mounted to the hinge housing member and a common shaft or axle can provide both a connector point and pivot point for the respective abductor member and pair of adjuster members. A fastening member can be mounted within the housing for radial movement towards the pivot point for releasably holding the respective adjuster members to define the limits of movement of the abductor member in a convenient manner. Each of the adjuster members can have an arcuate aperture into which a stop member journalled on the abductor member extends. An indicator lever can also be integrally formed on the outer perimeter of each of the adjuster members to permit manual manipulation by the operator and to define with a scale mounted on the housing member the degrees of movement desired for the abductor member.

In an alternative embodiment, the hinge housing member can have an arcuate opening with indicator members extending through the arcuate opening from each of the adjuster members. This eliminates the exterior indicator guides for a more compact configuration.

An operator can easily and accurately adjust the degree of movement without any additional tools to maintain specific limits of movements for the orthosis. The abductor member can be axially aligned with the plate or bar of the hinge housing member in a relatively economical configuration.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings.

DETAILED DESCRIPTION OF THE PREFERRED EMBODIMENTS

The following description is provided to enable any person skilled in the medical field to make and use the invention and sets forth the best modes contemplated by the inventor of carrying out his invention. Various modifications, however, will remain readily apparent to those skilled in the art, since the generic principles of the present invention have been defined herein specifically to provide an improved knee orthosis having an orthopedic knee hinge assembly that can be economically manufactured and easily used.

The orthopedic hinge assembly of the present invention is disclosed in preferred embodiments as a knee hinge assembly for an orthopedic brace. It can be readily recognized that the orthopedic hinge assembly of the present invention can also be utilized for other forms of orthosis wherein an abductor member requires controlled movement. Thus, the hinge assembly of the present invention can be employed in other orthosis structures than a knee hinge assembly so that a patient can enjoy the benefits of the present invention.

Figure 1:
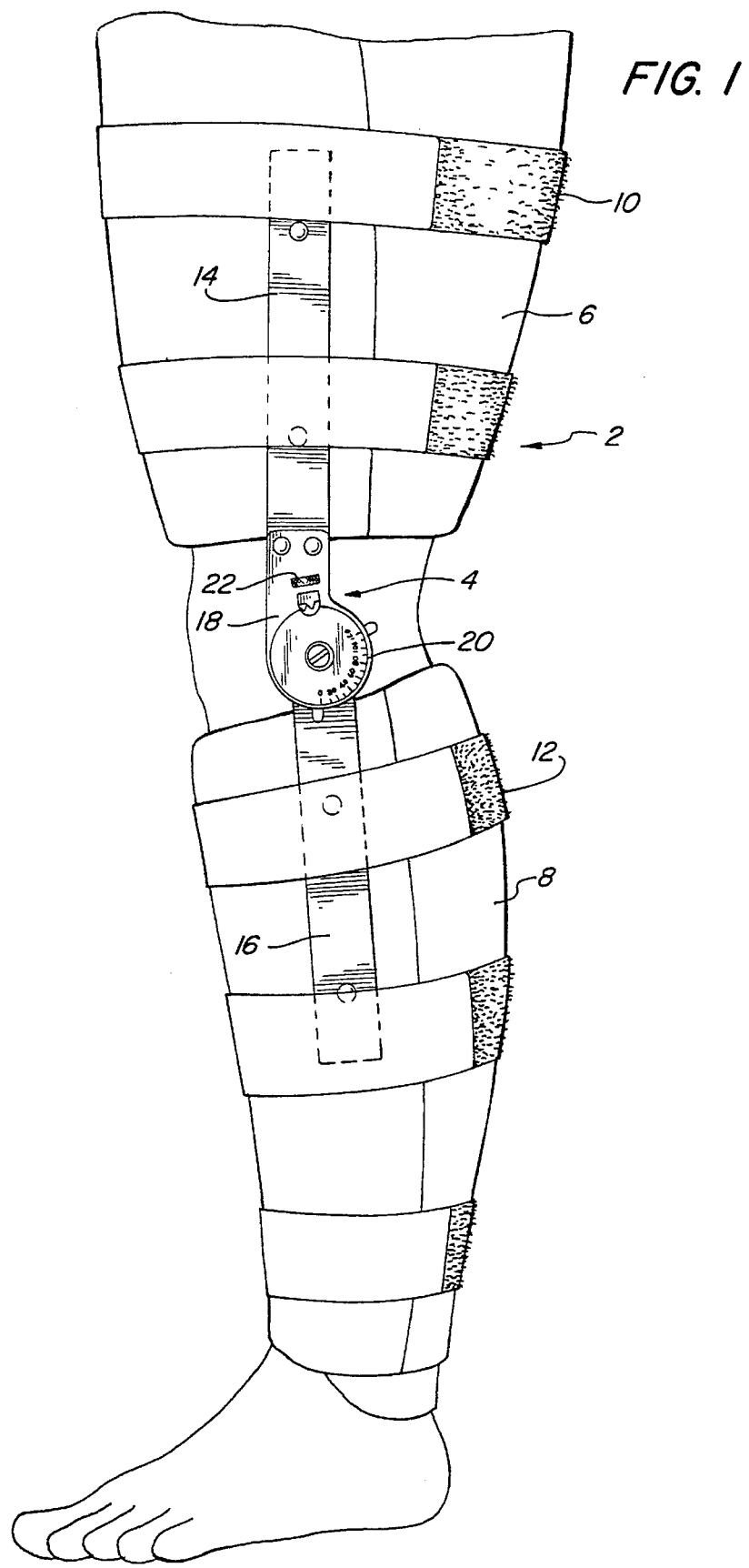
FIG. 1 is a side perspective view of a knee orthosis of the present invention.

Referring to FIG. 1, a perspective view of the improved knee orthosis 2 is disclosed using the orthopedic hinge assembly 4 of the present invention. The knee orthosis 2 includes an upper brace portion 6 and a lower brace portion 8. As can be readily appreciated, the particular configurations of the brace portions 6 and 8 can be varied, depending upon the particular application. For example, if the knee orthosis 2 is used for sport activities to provide a controlled range of motion, different configurations of the upper and lower brace portions can be accommodated including even bifurcation of the brace portions into separate strap members. The upper brace portion 6 can be prefabricated from a perforated polyethylene shell that has been lined with a finished neoprene foam and a pair of shells is usually provided. The upper brace portion 6 in the disclosed embodiment has a configuration for treatment of a left knee injury, such as repair of cartilage damage. While not shown, a pair of hinge assemblies 4 are used, are on either side of the brace portions. Obviously, the present invention can be modified for a right knee application. The upper brace portion 6 can have left and right shells that are interconnected with one or more flexible webs which can be adjustable with a Velcro™ belt or pair of belts 10 of a conventional hook and nap configuration.

The lower brace portion 8 is also formed with a pair of polyethylene shells to capture the inner and outer calf portions of a patient. The brace shells are also held together by a pair of movable attachable hook and nap belts 12.

The hinge assembly 4 is shown attached to metal plates or bars 14 and 16 which can be appropriately configured to maximize the support and interconnection with the upper portion 6 and the lower brace portion 8. The particular configuration of the plates 14 and 16 are illustrative only and can be modified as known in the medical field to accommodate a particular fastening of the respective brace portion. Further description of the upper brace portion 6 and the lower brace portion 8 are not believed to be necessary to understand the purposes of the present invention in the environment of knee orthosis 2. Various modifications of the brace portions can be made by a person of skill in this field and numerous examples currently exist in the commercial field.

The hinge assembly 4 includes a housing member 18 having, on an exterior surface a graded degree index scale 20, e.g., from 0 to 120 degrees to enable the patient or a technician to readily adjust the degree of extension and flexion of an abductor member, such as the plate 16. A fastening mechanism can be adjusted by a manual knob 22 which is capable of releasing individual adjuster members, to be described to permit setting a desired position for defining the limits of movement of the abductor member 16.

Figure 4:
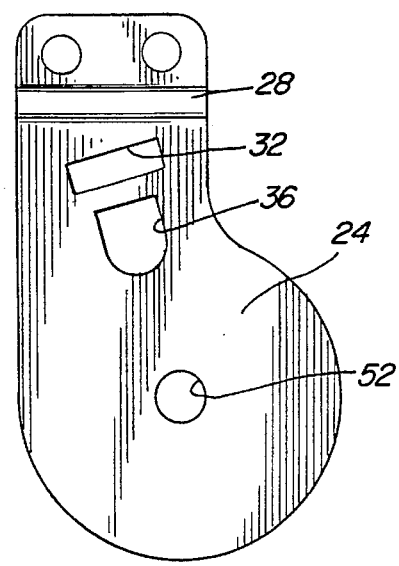
FIG. 4 is a plan view of housing plate.
Figure 5:
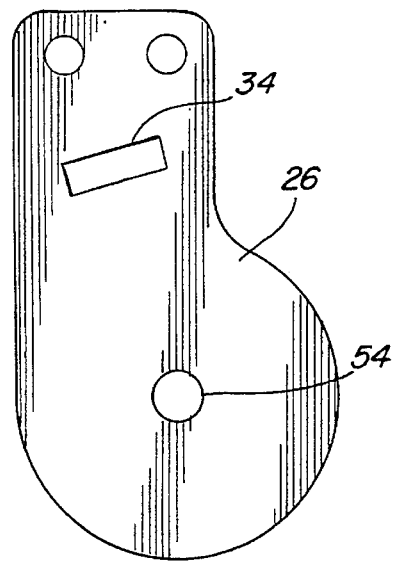
FIG. 5 is a plan view of another housing plate.

The hinge housing member 18 can be formed by a pair of flat metal plates, as shown, respectively, in FIGS. 4 and 5. Thus, a metal stamping operation can be used to form the hinge housing member 18 to reduce the cost of manufacturing. A outer housing member or plate 24 has a bent offset portion 28 so that the principal portion of the outside housing plate 24 is offset from and parallel to the inside housing plate 26 when they are fastened together by a rivet 30. Aligned rectangular apertures 32 and 34 are respectively positioned on the inner and outer housing plates 26 and 24 to accommodate a knurled knob member 22.

Figures 2, 3:
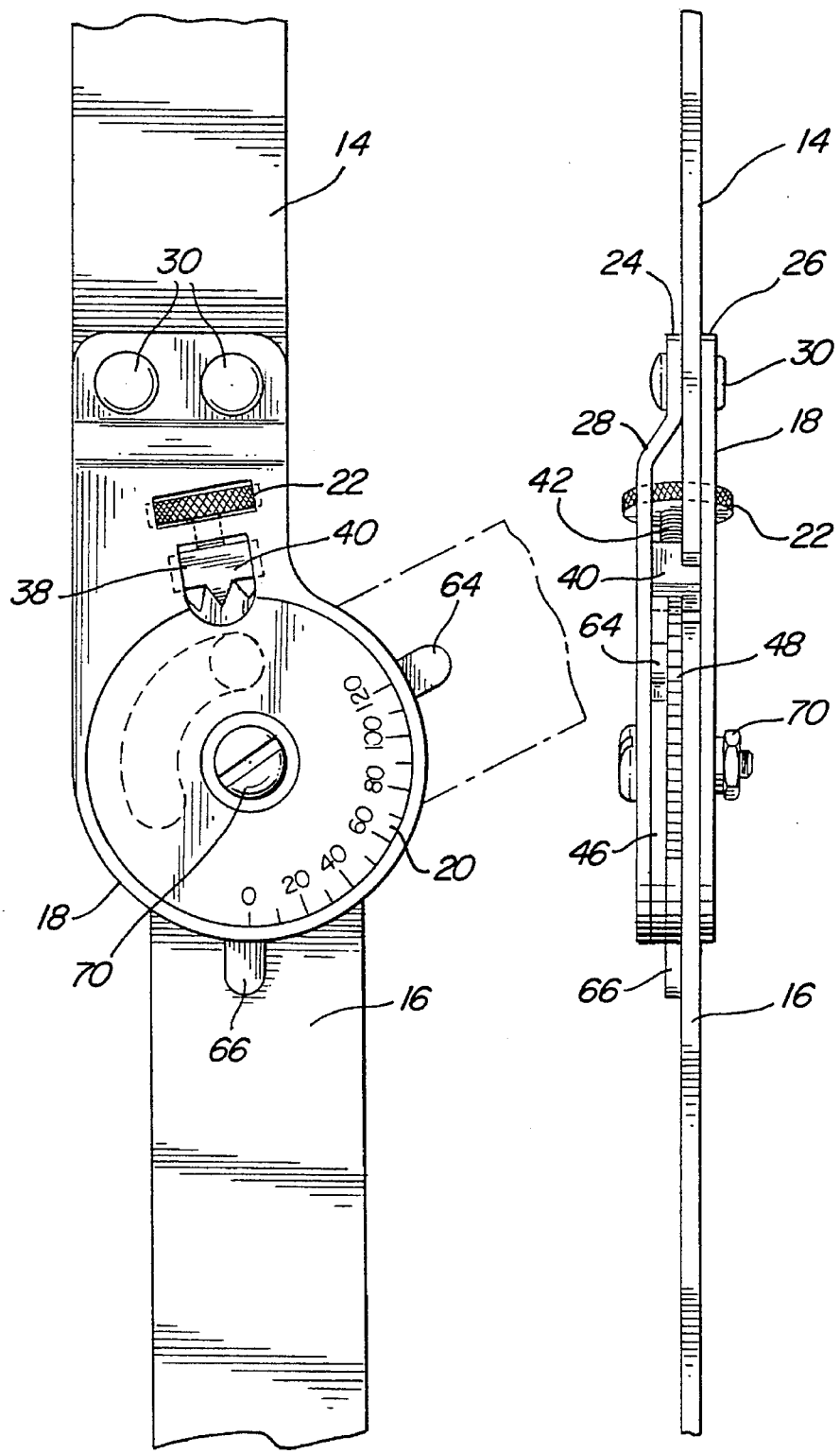
FIG. 2 is a partial plan view of an orthopedic knee hinge assembly of the present invention.
FIG. 3 is a side view of the orthopedic knee hinge assembly of the present invention.

A view window 36 in the outer housing plate 26 enables the operator to monitor the position of a fastener member assembly 38 which is operatively connected to the knob member 22, see FIG. 2. The fastener member 38 can contain a pointed tooth 40 which can travel along a predetermined path. The tooth member 40 has a threaded bore so that it can be driven by a threaded shaft 42 connected to the knob member 22.

Figure 6:
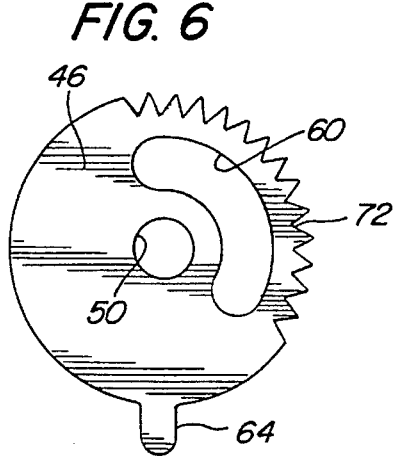
FIG. 6 is a plan view of an adjuster member.
Figure 8:
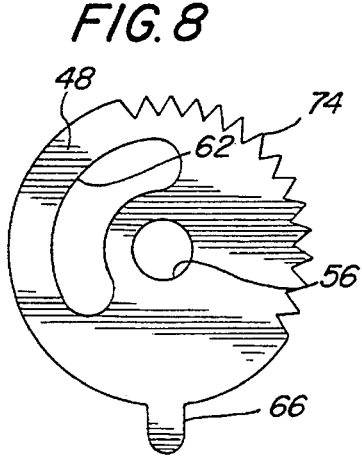
FIG. 8 is a plan view of another adjuster member.
Figure 11:
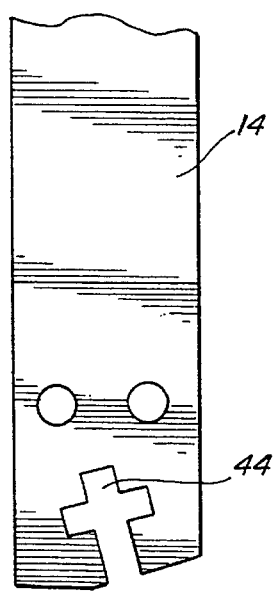
FIG. 11 is a partial plan view of an end of a plate or bar.
Figure 12:
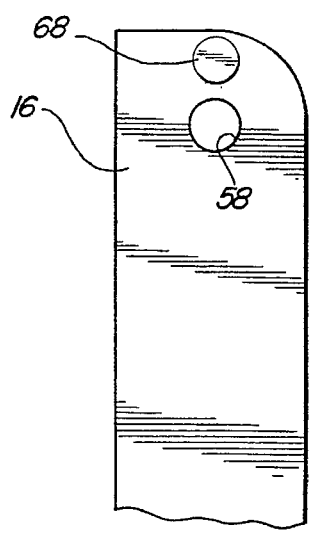
FIG. 12 is a partial plan view of one end of the abductor member.

Referring to FIG. 11, the lower end of the upper plate 14 is disclosed having a cross-shaped aperture 44 which, when mounted between the inside and outside housing plates 26 and 24, provide a journal opening for movement of the fastening member assembly 38. As can be seen, a pair of rivets can pass through appropriate apertures in the respective housing plate and upper plate. Mounted between the inside and outside housing plates is the lower abductor plate 16 and a pair of adjuster members 46 and 48, as seen in, respectively, FIGS. 6 and 8. The first adjuster member 46 has a central bore 50 which can be aligned with the central bore 52 and 54 in the respective outer and inside housing plates 24 and 26. The second adjuster member 48 also has a bore 56 at a complementary location. Referring to FIG. 12, a bore 58 is provided on the abductor member 16.

Figure 7:
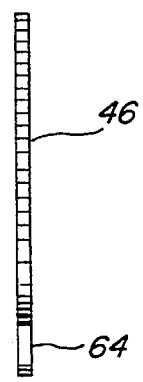
FIG. 7 is side view of the adjuster member of FIG. 6.
Figure 9:
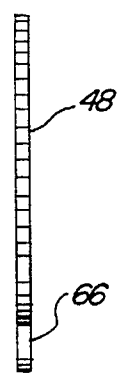
FIG. 9 is a side view of the adjuster member of FIG. 8.

The first adjuster member 46 has an arcuate aperture 60 that extends approximately 120 degrees about the bore 50 at a fixed radial distance. Likewise, the second adjuster member 48 has an arcuate aperture 62 and an identical radial location to also extend about its bore 56 at approximately 120 degrees. Each of the respective first and second adjuster members have peripheral complementary indentations or gear teeth 72 and 74 on their outer surface, as can be seen, respectively, in FIG. 6 and the side view of FIG. 7 for the first adjuster member 46, and in FIG. 8 and the side view of FIG. 9 for the second adjuster member 48.

Figure 10:
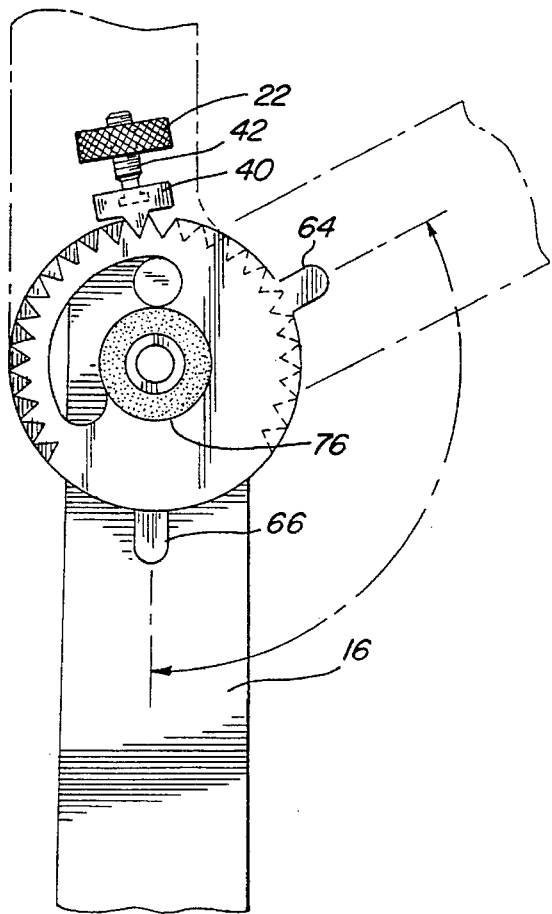
FIG. 10 is a partial view of elements of a first embodiment of the present invention.
Figure 13:
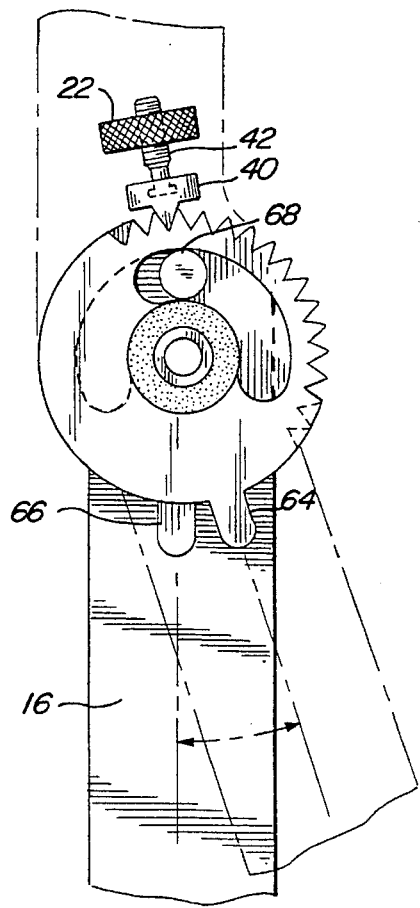
FIG. 13 is a partial view of elements of a first embodiment.

An indicator tab 64 extends radially outward on the first adjuster member 46 while another indicator tab 66 extends radially outward on the second adjuster member 48. Referring to FIG. 12, a stop member 68 can either be screwed into or integrally formed with the abductor member 16. The position of the stop member 68 and its dimension is complementary to the width of the arcuate openings 60 and 62. As can be appreciated, the position of the stop member 68 and the arcuate openings 60 and 62 can be re-oriented, e.g., jointly moved about the pivot point while still maintaining an operative relationship. When a shaft 70 is secured through, respectively, the bore 52 and 54 of the outer and inner housing plates 24 and 26, the shaft also will extend through the bore opening 58 and the bore openings 50 and 56 of the respective adjuster members. In commercial embodiments, a riveted shaft (not shown) would be preferably used. The stop member 58 will likewise extend through the arcuate opening 60 and 62. As can be appreciated, by relative movement of the first and second adjuster members the overlapping corresponding opening of the arcuate apertures 60 and 62 can define the limits of travel of the stop member 68. Thus, as shown in FIG. 10, when the indicator tabs 64 and 66 are positioned at the extremes of the gradient index scale 20, as shown in FIG. 2 and FIG. 10, the maximum degree of movement of the abductor member 16 is provided. In this example, 120 degrees are shown so that the abductor member 16 can rotate to the phantom position, shown in FIG. 10. Complementary indentations or gear teeth 72 and 74 are provided for a portion of the outer perimeter of the respective adjuster members 46 and 48. The fastener member assembly 38 can be manually manipulated so that by turning of the knob member 22, the tooth member 40 can be retracted to permit relative movement of the respective adjuster members 46 and 48. When this occurs, the operator can then arbitrarily set the range or limits of movement of the abductor member 16. Thus, as seen in FIG. 13, the operator has readjusted the relative position of the adjuster members 46 and 48 so that the respective tab members 66 and 64 are close together. As a result of this configuration, the stop member 68 is captured with a limited range of movement for the abductor member 16.

A washer 76 is disclosed, respectively, in FIGS. 10 and 13 for mounting between the first adjuster member and the outer housing plate 24.

Figure 14:
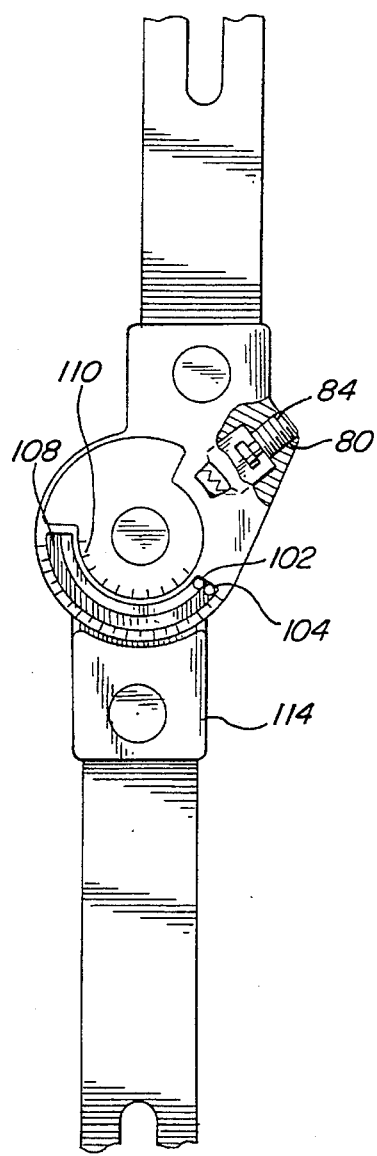
FIG. 14 is a partial cross-sectional view of an alternative embodiment of a hinge assembly of the present invention.
Figure 15:
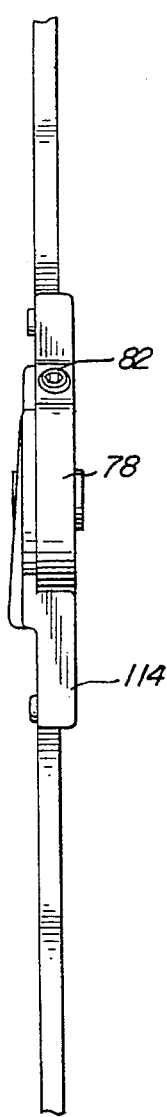
FIG. 15 is a side view of the embodiment of FIG. 14.

Referring to FIGS. 14 and 15, an alternative embodiment of the present invention is disclosed. The functioning of this embodiment is similar to the first embodiment, except that a housing member 78 is formed from a casting and the fastener member assembly 80 is adjusted by an Allen wrench that can fit into an aperture in the appropriate end 82 of a threaded shaft 84.

Figure 16:
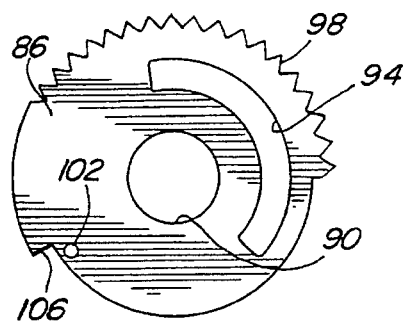
FIG. 16 is a plan view of an alternative embodiment of an adjuster member.
Figure 17:
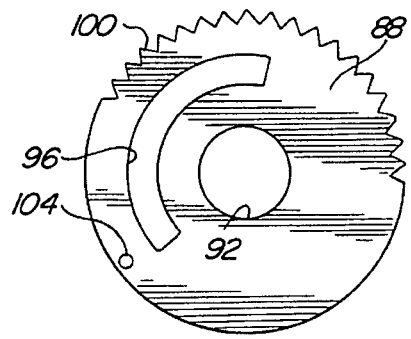
FIG. 17 is a plan view of another alternative embodiment of an adjuster member.

FIGS. 16 and 17 show the respective adjuster members 86 and 88. As with the previous adjuster members, central bores 90 and 92 are provided along with arcuate apertures 94 and 96. Also gear teeth 98 and 100 of a complementary configuration are provided on the outer periphery of each of the adjuster members.

The principal difference in this configuration from the earlier arrangement is the elimination of the radially extending outward indicator tabs 64 and 66. In this embodiment, indicator pins 102 and 104 rise from the respective surfaces of the adjuster members 86 and 88. To accommodate the indicator pin 104 on the adjuster member 88, a stepped portion 106 of the outer periphery 106 on the adjuster member 86 is provided so that the indicator pin 104 can rotate without interference, as seen in FIG. 14. An arcuate housing opening 108 is provided to permit access to respective indicator pins 102 and 104. In this embodiment, the indicator pins 102 and 104 are protected while the exterior of the housing member 108 does not provide any extending indicator tabs. The operation of this embodiment of the invention is the same in that the fastener member 80 can be adjusted with an Allen wrench (not shown) to release the respective adjustment members 86 and 88 so that the indicator pins 102 and 104 can be appropriately set relative to the graded index scale 110.

Figure 18:
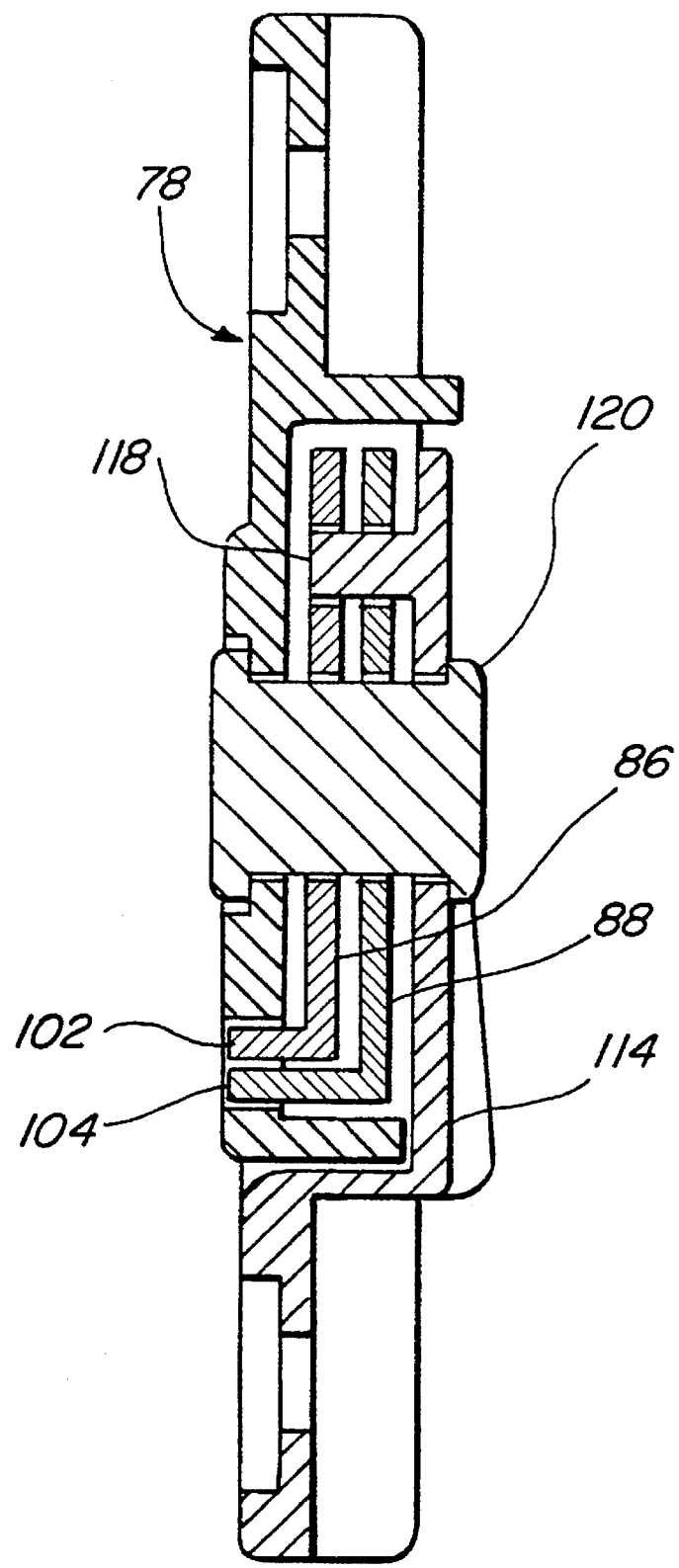
FIG. 18 is a cross-sectional view of the alternative embodiment of a hinge assembly.

Referring to FIG. 18, a cross-sectional view of the present invention is shown with a cast hinge housing 78 and a cast abductor member 114. The adjuster members 86 and 88 are journalled on a rivet shaft member 120 that also attaches the hinge housing 78 and abductor member 114 together for relative movement. The abductor member 114 has an integral stop member 118 that is limited in movement by the arcuate openings of the adjuster members 86 and 88. The positions of the arcuate openings are adjustable by the indicator pins 102 and 104 when the adjuster members are released by the fastener member 80.

After the upper brace portion 6 has been appropriately affixed to the patient (e.g. a prefabricated configuration can be appropriately adjusted subjectively to the patient's body) and the lower brace portion 8 has likewise been adjusted to the calf of the patient, then the extent of flexion and extension of the abductor member 16 can be easily set after a fastener member 38 has been rotated to release a pair of adjuster members. In the first embodiment, the adjuster tab 64 and 66 can be appropriately set, while in the second embodiment, the indicator pins 104 and 106 can be appropriately set to define a range of movement of a stop member 38. In the first embodiment, there is no requirement of any additional tools, while in the second embodiment, an Allen wrench can be utilized to release the fastener member. As can be readily appreciated, the patient can even be instructed to set the limit of travel of the brace member himself or herself by monitoring the appropriate index scale and adjusting the appropriate indicator tabs or pins.

While the preferred embodiment of the present invention uses aluminum plates, it can be readily appreciated that other material, such as plastic, or even stainless steel can be utilized within the scope of the present invention. By using aluminum that can be appropriately stamped out from aluminum stock, a relatively compact and inexpensive hinge assembly can be provided to address the majority of knee orthosis requirements.

While a knee orthosis has been shown as the preferred embodiment of a hinge assembly of the present invention, it can be readily appreciated that the hinge assembly itself can be applied to other orthosis structures for others limbs of a patient so that they can enjoy the economic benefits of the present invention.

Those skilled in the art will appreciate that various adaptations and modifications of the just-described preferred embodiments can be configured without departing from the scope and spirit of the invention. Therefore, it is to be understood that, within the scope of the appended claims, the invention may be practiced other than as specifically described herein.

What is claimed is:

1. An orthopedic hinge assembly for interconnecting an upper and a lower portion of a brace, comprising:

a housing member;

means on the housing member for enabling attachment to a brace portion;

an abductor member movably mounted on the housing member;

means on the abductor member for enabling attachment to another brace portion;

a first adjuster member movably mounted to the housing member;

a second adjuster member movably mounted to the housing member, wherein the abductor member, first adjuster member, and second adjuster member are pivotally mounted about a common pivot point;

a stop member extending through the respective first and second adjuster members; and means for removably fastening the first and second adjuster members together to define a fixed relative movement of the abductor member including a fastener member journalled in the housing member for radial movement relative to the common pivot point, whereby an operator can move the first and second adjuster members relative to each other to a desired position to define the limits of movement of the abductor member and then fasten the first and second adjuster members together so that the adjuster members are fixedly attached together.

2. The orthopedic hinge assembly of claim 1, wherein each adjuster member has complementary indentations on an outer perimeter surface.

3. The orthopedic hinge assembly of claim 2, wherein the means for removably fastening the adjuster members is a fastener member which is dimensioned to overlap the outer perimeter surface of each adjuster member and to removably engage their indentations.

4. The orthopedic hinge assembly of claim 2, wherein each adjuster member has an arcuate aperture through which the stop member extends.

5. The orthopedic hinge assembly of claim 2, wherein each adjuster member has a thin flat disk configuration.

6. The orthopedic hinge assembly of claim 2, wherein each adjuster member has an indicator that extends through the housing member to permit operator movement to adjust the limits of movement.

7. The orthopedic hinge assembly of claim 2, wherein each adjuster member is rotatably mounted within the housing member.

8. The orthopedic hinge assembly of claim 1, wherein the housing member comprises a pair of flat plate members fastened together and positioned on either side of the abductor member, first adjuster member and second adjuster member.

9. The orthopedic hinge assembly of claim 1, wherein the housing member is a unitary metal casted part.

10. The orthopedic hinge assembly of claim 1, wherein the housing member has an arcuate opening on one side and the first and second adjuster members include respective indicators that are adjustable through the arcuate opening to define the limits of movement.

11. The orthopedic hinge assembly of claim 1, wherein the housing member comprises a pair of flat plates, the abductor member is a flat plate and the first and second adjuster members are flat disks.

12. The orthopedic hinge assembly of claim 11, wherein the housing member, abductor member and first and second adjuster members are connected together by a common axle.

13. The orthopedic hinge assembly of claim 1 wherein the means for removably fastening is permanently mounted on the housing members.

14. The orthopedic hinge assembly of claim 1 wherein the means for removably fastening includes a rotatable knob manually adjustable and rotatably secured to extend on either side of the housing member.

15. An orthopedic hinge assembly for interconnecting an upper and a lower portion of a brace, comprising:

a housing member;

means on the housing member for enabling attachment to a brace portion;

an abductor member movably mounted on the housing member;

means on the abductor member for enabling attachment to another brace portion;

a first adjuster member movably mounted to the housing member;

a second adjuster member movably mounted to the housing member;

a stop member extending through the respective first and second adjuster members; and means for removably fastening the first and second adjuster members together to define relative movement of the abductor member whereby an operator can move the first and second adjuster members relative to each other to a desired position to define the limits of movement of the abductor member and then fasten the first and second adjuster members together so that the adjuster members are fixedly attached together, wherein the housing member has an arcuate opening on one side and the first and second adjuster members include respective indicators that are adjustable through the arcuate opening to define the limits of movement.

16. The orthopedic hinge assembly of claim 15, wherein the abductor member, first adjuster member and second adjuster member are pivotally mounted about a common pivot point.

17. The orthopedic hinge assembly of claim 16, wherein the fastener member is journalled in the housing member for radial movement relative to the common pivot point.

18. The orthopedic hinge assembly of claim 15, wherein each adjuster member has complementary indentations on an outer surface.

19. The orthopedic hinge assembly of claim 18 wherein the means for removably fastening the adjuster members is a fastener member which is dimensioned to overlap the outer surface of each adjuster member and to removably engage their indentations.

20. An orthopedic hinge assembly for interconnecting an upper and a lower portion of a brace, comprising;

a housing member formed of a pair of thin metal plates;

means on the housing member for enabling attachment to a brace portion;

a flat plate abductor member movably mounted on the housing member;

means on the abductor member for enabling attachment to another brace portion;

a first flat metal plate adjuster member movably mounted to the housing member for rotation about an axis of rotation, the first plate adjuster member having a first aperture radially offset from the axis of rotation;

a second metal flat plate adjuster member movably mounted to the housing member for rotation about the axis of rotation, the second plate adjuster member having a second aperture radially offset from the axis of rotation and at least partially overlapping the first aperture;

a stop member extending through the respective first and second plate adjuster members; and means for removably fastening the first and second plate adjuster members together to define a fixed relative movement of the abductor member whereby an operator can move the first and second adjuster members relative to each other to a desired position to define the limits of movement of the abductor member by adjusting the amount of overlap of the respective first and second apertures to limit the movement of the stop member, and then fasten the first and second plate adjuster members together so that the adjuster members are fixedly attached together.

21. The orthopedic hinge assembly of claim 20, wherein the means for removably fastening the adjuster members is a fastener member which is dimensioned to overlap the outer surface of each adjuster member and to removably engage their indentations.

22. The orthopedic hinge assembly of claim 21, wherein each adjuster member has an indicator member that extends through the housing member to permit operator movement to adjust the limits of movement.

23. An orthopedic hinge assembly for interconnecting an upper and a lower portion of a brace, comprising:

a housing member;

means on the housing member for enabling attachment to a brace portion;

an abductor member movably mounted on the housing member;

means on the abductor member for enabling attachment to another brace portion;

a first adjuster member movably mounted to the housing member for rotation about an axis of rotation, the first adjuster member having a first aperture radially offset from the axis of rotation;

a second adjuster member movably mounted to the housing member for rotation about the axis of rotation, the second adjuster member having a second aperture radially offset from the axis of rotation and at least partially overlapping the first aperture;

a stop member extending through the respective first and second apertures of the adjuster members; and means for removably fastening the first and second adjuster members together to define a fixed relative movement of the abductor member whereby an operator can move the first and second adjuster members relative to each other to desired positions to define the limits of movement of the abductor member by adjusting the amount of overlap of the respective first and second apertures to limit the movement of the stop member, and then fasten the first and second adjuster members together so that the adjuster members are fixedly attached to the housing member during operative movement of the abductor member.

24. The orthopedic hinge assembly of claim 23 wherein the means for removably fastening includes a fastener member which is permanently mounted in the housing member for movement along a fixed predetermined path for engagement with the first and second adjuster members.

25. The orthopedic hinge assembly of claim 24 wherein the first and second adjuster members have outer perimeter indentations and the fastener member can releasably engage the indentations on both adjuster members.

26. The orthopedic hinge assembly of claim 24 wherein the housing member is bifurcated and the first and second adjuster members are movably mounted within the housing member.

27. The orthopedic hinge assembly of claim 26 wherein the fastener member is mounted within the housing member for movement within a plane parallel to a plane containing the movement of the abductor member.

28. The orthopedic hinge assembly of claim 24 wherein each adjuster member includes an indicator member that extends through the housing member to permit manual adjustment by the operator to define the limits of movement of the abductor member.

* * * * *